United States Patent
Koike et al.

(10) Patent No.: US 7,862,625 B2
(45) Date of Patent: Jan. 4, 2011

(54) ONE-PART HAIR DYE COMPOSITION

(75) Inventors: Kenzo Koike, Tokyo (JP); Atsuko Ebato, Tokyo (JP)

(73) Assignee: Kao Corporation, Tokyo (JP)

( * ) Notice: Subject to any disclaimer, the term of this patent is extended or adjusted under 35 U.S.C. 154(b) by 2 days.

(21) Appl. No.: 12/303,607

(22) PCT Filed: Jun. 7, 2007

(86) PCT No.: PCT/JP2007/000613

§ 371 (c)(1),
(2), (4) Date: Dec. 5, 2008

(87) PCT Pub. No.: WO2007/141919

PCT Pub. Date: Dec. 13, 2007

(65) Prior Publication Data

US 2010/0125956 A1  May 27, 2010

(30) Foreign Application Priority Data

Jun. 7, 2006  (JP) .............................. 2006-159130

(51) Int. Cl.
  *A61Q 5/10* (2006.01)
(52) U.S. Cl. ...................... 8/405; 8/435; 8/574; 8/604; 8/670
(58) Field of Classification Search .................. 8/405, 8/435, 574, 604, 670
  See application file for complete search history.

(56) References Cited

U.S. PATENT DOCUMENTS

| | | | |
|---|---|---|---|
| 4,208,183 A | 6/1980 | Grollier et al. | |
| 4,900,326 A | 2/1990 | Grollier | |
| 5,021,067 A * | 6/1991 | Grollier | 8/409 |
| 5,704,949 A | 1/1998 | Prota et al. | |
| 7,083,655 B2 | 8/2006 | Pratt et al. | |
| 2006/0000032 A1 | 1/2006 | Knuebel et al. | |

FOREIGN PATENT DOCUMENTS

| | | |
|---|---|---|
| CN | 1599590 A | 3/2005 |
| DE | 10120915 | 11/2001 |
| EP | 0 553 937 A1 | 3/1993 |
| EP | 1 254 650 A2 | 11/2002 |
| EP | 1 430 873 A1 | 6/2004 |
| EP | 1 433 470 A1 | 6/2004 |
| JP | 57-192310 | 11/1982 |
| JP | 8-32618 | 3/1996 |
| JP | 11-12139 | 1/1999 |
| JP | 2002-322038 | 11/2002 |
| JP | 2003-55175 | 2/2003 |
| JP | A-2003-342139 | 12/2003 |
| WO | WO 92/14441 | 9/1992 |
| WO | WO 99/66890 | 12/1999 |
| WO | WO 2004/024109 A1 | 3/2004 |

OTHER PUBLICATIONS

Dialog Database, Derwent Accession No. 2004-490110/200447, English language abstract for EP 1433470, Jun. 20, 2004.
Dialog Database, Derwent World Patent Index File 351 Accession No. 10376798, English language abstract for WO 1999/066890 A1, published Dec. 29, 1999.
Dialog Database, Derwent World Patent Index File 351 Accession No. 14485871, English language abstract for WO 2004/024109 A1.
International Search Report for International Application No. PCT/JP2007/000613, mailed on Jul. 10, 2007, Japanese Patent Office, Tokyo, Japan.
Koike et al., U.S. Appl. No. 12/303,604 (Natl. Phase of PCT/JP2007/000612; Int'l Filing Date: Jun. 7, 2007).
Koike et al., U.S. Appl. No. 12/303,610 (Natl. Phase of PCT/JP2007/000614; Int'l Filing Date: Jun. 7, 2007).
Dialog Database, Derwent World Patent Index File 351 Accession No. 4239691, English language abstract for JP 08-32618 (JP 1996032618), published Mar. 29, 1996.
Dialog Database, JAPIO File 347 Accession No. 7453523, English language abstract for JP 2002-322038, published Nov. 11, 2002.
Dialog Database, Derwent Accession No. 9688938, English language abstract for JP 11-12139, published Jan. 19, 1999.

(Continued)

*Primary Examiner*—Eisa B Elhilo
(74) *Attorney, Agent, or Firm*—Sterne, Kessler, Goldstein & Fox P.L.L.C.

(57) ABSTRACT

Provided is a one-part hair dye composition containing (A) one or two or more compounds represented by the formula (1), (B) an antioxidant composed of a combination of ascorbic acid or salt thereof and sulfurous acid or salt thereof, (C) a nonionic surfactant, and (D) a thickening polymer; and having a pH of from 8 to 11; and a method of controlling hair color by adjusting an (ascorbic acid or salt thereof)/(sulfurous acid or salt thereof) weight ratio in Component (B) of the composition:

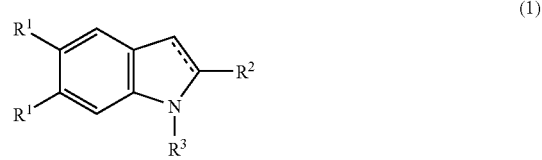

(1)

(wherein, a broken line: the presence or absence of a π bond, $R^1$: OH or acetoxy, $R^2$: H, —COOR (R: H, $CH_3$ or $C_2H_5$) or —COO⁻X⁺ ($X^+$: cation), and $R^3$: H, acetyl, $CH_3$ or $C_2H_5$).

16 Claims, No Drawings

OTHER PUBLICATIONS

Dialog Database, Derwent Accession No. 14034115 , English language abstract for JP-A-2003-342139, published Dec. 3, 2003.

International Preliminary Report on Patentability for PCT/JP2007/000613 (the PCT phase of U.S. Appl. No. 12/303,607), issued Jan. 13, 2009, with the English language translation of the Written Opinion, The International Bureau of WIPO, Geneva, Switzerland.

Office action mailed Mar. 10, 2010 for U.S. Appl. No. 12/303,604, and Amendment and Reply to same filed Aug. 18, 2010.

Office action mailed May 13, 2010 for U.S. Appl. No. 12/303,610, and Amendment and Reply to same filed Aug. 18, 2010.

Dialog Database, Derwent World Patent Index File 352 Accession No. 2002-076390/200211, English language abstract for DE 10120915 Al, published Nov. 15, 2001.

Patent Abstracts of Japan, English language abstract of JP 57-192310, published Nov. 26, 1982.

Dialog Database, Derwent World Patent Index File 351 Accession No. 6077403, English language abstract for WO 1992/014441 Al, published Sep. 3, 1992.

International Preliminary Report on Patentability for PCT/JP2007/000612 (the PCT phase of U.S. Appl. No. 12/303,604), issued Jan. 13, 2009, with the English language translation of the Written Opinion, The International Bureau of WIPO, Geneva, Switzerland.

International Preliminary Report on Patentability for PCT/JP2007/000614 (the PCT phase of U.S. Appl. No. 12/303,610), issued Jan. 13, 2009, with the English language translation of the Written Opinion, The International Bureau of WIPO, Geneva, Switzerland.

Office action for CN 200780020625.2, mailed Jul. 16, 2010 from the Patent Office of the People's Republic of China, Beijing, China.

* cited by examiner

ONE-PART HAIR DYE COMPOSITION

FIELD OF THE INVENTION

The present invention relates to a one-part hair dye composition capable of dyeing hair into different hair colors without using a coupler.

BACKGROUND OF THE INVENTION

Air-oxidative hair dye compositions using a melanin precursor such as indoles or indolines have conventionally been known (refer to, for example, Patent Documents 1 to 3). These hair dyes however require use of a coupler in combination with a melanin precursor in order to adjust the final hair color.
Patent Document 1 JP-B-8-32618
Patent Document 2 JP-A-2003-55175
Patent Document 3 JP-A-2002-322038

DISCLOSURE OF THE INVENTION

In one aspect of the present invention, there is provided a one-part hair dye composition, having a pH of from 8 to 11, containing the following components (A) to (D):

(A) one or two or more compounds represented by the following formula (1):

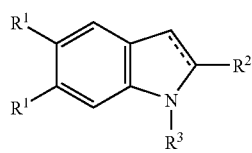

(1)

wherein, a broken line represents the presence or absence of a π bond, $R^1$ represents a hydroxy or acetoxy group, $R^2$ represents a hydrogen atom, —COOR (wherein, R represents a hydrogen atom, methyl group or ethyl group) or —COO$^-$X$^+$ (wherein, X$^+$ represents a cation), and $R^3$ represents a hydrogen atom, acetyl group, methyl group or ethyl group, (B) an antioxidant composed of a combination of ascorbic acid or salt thereof and sulfurous acid or salt thereof, (C) a nonionic surfactant, and (D) a thickening polymer.

In another aspect of the present invention, there is also provided a method of adjusting a molar ratio of (ascorbic acid or salt thereof)/(sulfurous acid or salt thereof) in Component (B) of the above-described one-part hair dye composition, thereby controlling the hair color dyed therewith.

MODE FOR CARRYING OUT THE INVENTION

The present invention relates to an air-oxidative hair dye composition capable of dying hair into different hair colors without using a coupler.

The present inventors have found that the above-described problem of an air oxidative hair dye composition using a melanin precursor can be overcome by using a combination of two specific antioxidants, a nonionic surfactant and a thickening polymer.

The compound represented by the formula (1) and serving as Component (A) is an indole derivative or indoline derivative (melanin precursor) that is converted into a melanin pigment by oxidation. Examples of the compound represented by the formula (1) include 5,6-dihydroxyindole, 5,6-dihydroxyindole-2-carboxylic acid, 5,6-dihydroxyindolin and 5,6-dihydroxyindolin-2-carboxylic acid. They can be used either singly or in combination of two or more. Use of two or more of them in combination enables control of the color of hair dyed with the resulting composition. For dyeing hair into a natural color, use of 5,6-dihydroxyindole and 5,6-dihydroxyindole-2-carboxylic acid in combination is preferred. When they are used in combination, a molar ratio of them is preferably adjusted to fall within a range of from 50:50 to 999:1, more preferably from 80:20 to 99:1. The amounts of 5,6-dihydroxyindole and 5,6-dihydroxyindole-2-carboxylic acid can be determined by reversed phase HPLC.

For the preparation of the compound represented by the formula (1), DOPA derived from legume plants can also be employed. As the legume plants, *Mucuna* is preferred, with velvet beans (*Mucuna pruriens*), cowage (*Stizolobium hassjoo*), *Mucuna cochinchinensis* and *Mucuna japonica* being more preferred. Of these *Mucuna cochinchinensis* is even more preferred because of its availability and stable DOPA content.

A DOPA-containing extract can be obtained from these legume plants by subjecting, to solvent extraction, leaves, stems, tissues available by callus culture and the like as is or after drying and grinding. It can be used as a DOPA extract (in the form of a liquid, powder or paste) after heightening its content as needed by a proper separation means such as gel filtration, chromatography or precision distillation, or it can be used as a purified product of DOPA. From the viewpoint of cost, it is preferred to use it as an extract for enzyme treatment without purifying it. Use of DOPA having a purity of 80 wt. % or greater is preferred, with 95 wt. % or greater being more preferred. As the solvent used for extraction, those typically used for the extraction of plant components are usable. Examples include water, petroleum ether, n-hexane, toluene, di-chloroethane, chloroform, ether, ethyl acetate, acetone, methanol, ethanol, propanol, butanol, ethylene glycol, propylene glycol, and butylene glycol. They may be used in combination of two or more, but use of water or a mixed solvent of water and an organic solvent is preferred. In addition, the extraction solvent is adjusted to preferably acidic or weakly acidic pHs, more specifically, to from pH 2 to 7, more preferably from pH 3 to 6. For the pH adjustment, an organic acid or inorganic acid is used. During extraction, typical extraction conditions can be employed. For example, the above-described plant may be dipped or heated under reflux for from several hours to several weeks at from 3 to 100° C.

Alternatively, a commercially available *Mucuna* extract is usable. Examples of the commercially available product include *Mucuna* extract (from low purity to high purity products) available from Herbal Powers and LEVODOPA (a high-purity product, 98 wt. % or greater) available from Chengdu superman/Chengdu/China. Of these, LEVODOPA (a high-purity product, 98 wt. % or greater) derived from Chinese *Mucana cochinchinensis* is preferred from the view-points of economy and availability.

The total content of the compounds as Component (A) in the hair dye composition of the present invention is preferably from 0.05 to 5 wt. %, more preferably from 0.1 to 2 wt. % from the viewpoints of dyeing properties and stability.

The antioxidant as Component (B) is composed of ascorbic acid or salt thereof and sulfurous acid or salt thereof at a predetermined ratio. Examples of the salt of ascorbic acid or sulfurous acid include sodium salt.

In the present invention, the final hair color can be controlled by adjusting a molar ratio of (ascorbic acid or salt thereof)/(sulfurous acid or salt thereof) in Component (B). Specifically, hair can be dyed into from a reddish brown to brown color by adjusting the molar ratio to from 99/1 to 50/50; hair can be dyed into from a brownish gray to dark gray color by adjusting the molar ratio to from 49/51 to 31/69; and hair can be dyed into from a slightly bluish gray color by adjusting the molar ratio from 30/70 to 1/99.

The total content of Component (B) in the hair dye composition of the present invention is preferably from 0.01 to 5 wt. %, more preferably from 0.05 to 2 wt. %, even more preferably from 0.1 to 1 wt. % from the standpoints of dyeing properties and control of color tone. In addition, use of from 0.1 to 0.5 wt. % of ascorbic acid or salt thereof and from 0.1 to 0.5 wt. % of sulfurous acid or salt thereof in combination is preferred.

Examples of the nonionic surfactant as Component (C) include polyoxyalkylene alkyl ethers, polyoxyalkylene alkenyl ethers, higher fatty acid sucrose esters, polyglycerin fatty acid esters, higher fatty acid monoethanolamides or diethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkylamidoamine oxides. Of these, polyethoxylates of a secondary alcohol represented by the following formula (2):

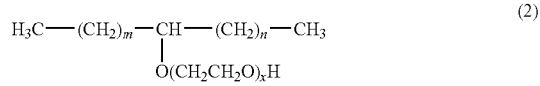

(2)

(wherein, m and n stand for a number so that the sum of m and n is from 7 to 25, preferably from 7 to 20, more preferably from 9 to 11, and x is a weight average and stands for a number from 6 to 16, preferably from 6 to 12, more preferably from 8 to 10) are preferred, with polyoxyethylene tridecyl ether ("Softanol 90", product of Nippon Shokubai, a compound of the formula (2) in which m+n=from 9 to 11 and x=9) being more preferred.

The above-described nonionic surfactants as Component (C) may be used either singly or in combination of two or more. The content of Component (C) in the hair dye composition of the present invention is preferably from 0.1 to 10 wt. %, more preferably from 0.5 to 5 wt. % from the view-points of usability and foaming properties.

The thickening polymer as Component (D) may be either a nonionic or ionic polymer. Examples of the nonionic thickening polymer include hydroxyethyl cellulose (for example, "SE-850", product of Daicel Chemical and "Cellosize HECQP52000H", product of Nagase Co.), sodium carboxymethyl-cellulose ("CMC Daicel 1220", product of Daicel Chemical), sodium hydroxyethylcellulose hydroxypropyl stearyl ether hydroxypropylsulfonate (for example, a compound described in Preparation Example 1 of JP-A-11-12139), hydroxypropylmethyl cellulose (for example, "Metolose 60SH-10000", product of Shin-Etsu Chemical), guar gum (for example, "Fiberon S", product of Dainippon Sumitomo Pharma), pullulan (for example, "Pullulan PI-20", product of Hayashibara Inc.), hydroxypropyl chitosan (for example, "Chitofilmer HV-10", product of Ichimaru Pharcos), chitosan•dlpyrrolidonecarboxylates (for example, "Chitomer PC", product of Union Carbide), polyvinylpyrrolidones ("Luviskol K-12", "Luviskol K-30", and "PVP K-120", each product of BASF), polyvinyl alcohol ("Gohsenol EG-40", product of Nippon Synthetic Chemical Industry), vinyl alcohol/vinylamine copolymer ("VA-120-HCl", product of Air Products and Chemicals), and high polymerization degree polyethylene glycol ("Polyox WSRN-60K", product of Union Carbide/Japan).

Examples of the anionic thickening polymers include polyacrylic acids ("Carbopol 941" and "Carbopol 981", each product of Noveon), acrylic acid/alkyl methacrylate copolymers ("Carbopol ETD2020", product of Noveon), hydrolysates of a lower alkyl vinyl ether/maleic anhydride copolymer partially crosslinked with a terminal-unsaturated diene compound or monoalkyl esters thereof ("Stabilize 06" and "Stabilize QM", each product of ISP), carrageenan (for example, "Soageena LX22" and "Soageena ML210", each product of Mitsubishi Rayon), xanthan gum (for example, "Echo gum T", product of Dainippon Sumitomo Pharma), welan gum (for example, "K1C376" and "K1A96", each product of Sansho), and hydroxypropyl xhantan gum (for example, "Rhaball gum EX", product of Dainippon Sumitomo Pharma).

As the cationic thickening polymers, those containing, in the side chain of the polymer chain thereof, an amino group or ammonium group or those containing a diallyl quaternary ammonium salt as a constituent unit, each in the form of an aqueous solution, are usable. Examples of them include a cationic cellulose derivative (for example, "Reoguard G" and "Reoguard GP", each product of Lion Corporation, "Polymer JR-125", "Polymer JR-400", "Polymer JR-30M", "Polymer LR-400", and "Polymer LR-30M", each product of Union Carbide, and "Celquat H-100" and "Celquat L-200", each product of National Starch & Chemical), a cationic guar gum derivative (for example, "Juguar C-13S" and "Juguar C-17", each product of Rhodia, and "Rhaball Gum CG-M", "Rhaball Gum CG-M7", and "Rhaball CG-M8M", each product of Dainippon Sumitomo Pharma), polymers or copolymers of a diallyl quaternary ammonium salt ("Merquat 100", "Merquat 280", "Merquat 295", and "Merquat 550", each, product of Calgon), and a quaternized polyvinylpyrrolidone derivative ("Gafquat 734", "Gafquat 755" and "Gafquat 755N", each product of ISP Japan).

Of these polymers, polysaccharide thickening polymers are preferred, with natural polymer type ones having a cellulose skeleton or xanthan gum skeleton being more preferred. These thickening polymers as Component (D) may be used either singly or in combination of two or more. The content of Component (D) in the hair dye composition of the present invention is preferably from 0.05 to 10 wt. %, more preferably from 0.1 to 3 wt. % from the viewpoints of coating properties and reduced dripping. The hair dye composition of the present invention has a viscosity of preferably from 100 to 8000 mPa·s, more preferably from 300 to 5000 mPa·s from the viewpoints of coating properties and reduced dripping. The term "viscosity" as used herein is a value determined after rotation for 1 minute at 6 rpm at 25° C. by using a Brookfield viscometer.

Although incorporation of a dye other than Component (A) in the hair dye composition of the present invention is not necessary, a direct dye typically employed for hair dyes may be incorporated further.

Examples of the direct dye include acid dyes, nitro dyes, disperse dyes, basic dyes and direct dyes described in JP-A-2003-342139. Examples of the acid dyes include Blue No. 1, Violet No. 401, Black No. 401, Orange No. 205, Red No. 227, Red No. 106, Yellow No. 203, and Acid Orange 3. Examples of the nitro dyes include 2-nitroparaphenylenediamine, 2-amino-6-chloro-4-nitrophenol, 3-nitro-p-hydroxyethylaminophenol, 4-nitroorthophenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, and N,N-bis-(2-hydroxyethyl)-2-nitroparaphenylenediamine. Examples of the disperse dyes include Disperse Violet 1, Disperse Blue 1 and Disperse Black 9, while those of the basic dyes include Basic Blue 99, Basic Brown 16, Basic Brown 17, Basic Red 76, Basic Red 51, Basic Yellow 57, Basic Yellow 87 and Basic Orange 31.

When the direct dye is added to the hair dye composition of the present invention, the content of it therein is preferably from 0.001 to 5 wt. %, more preferably from 0.01 to 3 wt. %.

The hair dye composition of the present invention may contain a melanin prepared by oxidation polymerization of one or two or more compounds represented by the formula (1). The melanin is preferably an oxidized polymer of at least one of 5,6-dihydroxyindole and 5,6-dihydroxyindole-2-carboxylic acid. From the viewpoints of stability and usability, a melanin having a molecular weight of 1000 or greater but not greater than 1000000 (measurable by "MALDITOF-MS", product of SHIMADZU Corporation), preferably a molecular weight of 2000 or greater but not greater than 10000, is used. Such a melanin has, retained therein, a portion of the functional groups derived from the compound represented by the formula (1). A melanin prepared using 5,6-dihydroxyindole-2-carboxylic acid or 5,6-dihydroxyindoline-2-carboxylic acid has therefore a carboxyl group and has an increased water solubility. Although a detailed reason has not been elucidated yet, the present inventors have found that when two melanin precursors are used upon the above-described polymerization, hair dyed with the resulting composition acquires a brown, gray or bluish gray color tone, different from a monotonous color such as black or gray produced by a temporary hair dye using a conventional melanin.

In order to prepare the hair dye composition containing such a melanin, a polymer of the compound represented by the formula (1), which has been prepared in advance, may be added to the hair dye composition of the present invention or a hair dye composition containing the compound of the formula (1) may be exposed to air during preparation to produce the melanin. The melanin thus produced has an effect of covering up the gray as a solid substance with a color ranging from black to brown so that it can complement the function, as a temporary hair dye, of the hair dye composition of the present invention. The content of it in the hair dye composition of the present invention is preferably from 0.01 to 50 wt. %, more preferably from 0.1 to 30 wt. %, even more preferably from 0.5 to 20 wt. %. In this case, it is preferred to use a film forming polymer further in combination.

In the hair dye composition of the present invention, a surfactant other than Component (C) may be incorporated.

Examples of such a surfactant include anionic surfactants such as alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, mono- or di-phosphate ester surfactants and sulfosuccinates; amphoteric surfactants such as imidazoline, carbobetaine, amidobetaine, sulfobetaine, hydroxysulfobetaine and amidosulfobetaine amphoteric surfactants; and cationic surfactants such as imidazoline ring-open type quaternary ammonium salts, mono(long chain) alkyl quaternary ammonium salts and di(long chain)alkyl quaternary ammonium salts. Examples of the counterion of the anionic residue of the above-described surfactants include alkali metal ions such as a sodium ion and a potassium ion; alkaline earth metal ions such as a calcium ion and a magnesium ion, an ammonium ion, and alkanolamines having 1 to 3 alkanol groups with 2 or 3 carbon atoms (such as monoethanolamine, diethanolamine, triethanolamine and triisopropanolamine). Examples of the counterion of the cationic residue include halide ions such as a chloride ion, a bromide ion and an iodide ion, a methosulfate ion and a saccharinate ion.

These surfactants other than Component (C) may be used either singly or in combination of two or more. Their content in the hair dye composition of the present invention is preferably from 0.1 to 30 wt. %, more preferably from 0.5 to 15 wt. %.

In the hair dye composition of the present invention, a linear aliphatic alcohol having from 12 to 24 carbon atoms can be incorporated in order to improve foam quality and usability. Specific examples thereof include myristyl alcohol, cetyl alcohol, stearyl alcohol, arachyl alcohol, and behenyl alcohol, with stearyl alcohol and behenyl alcohol being more preferred.

These linear aliphatic alcohols may be used either singly or in combination of two or more. Their content in the hair dye composition of the present invention is preferably from 0.01 to 10 wt. %, more preferably from 0.1 to 7 wt. %, even more preferably from 0.5 to 5 wt. %.

In the hair dye composition of the present invention, an alkali agent typically employed for hair dyes may be incorporated. Examples thereof include aqueous ammonia, alkanolamines such as mono-, di- or triethanolamine; alkyl- or aralkylamines such as butylamine and benzylamine; basic amino acids such as arginine, lysine and histidine; and inorganic bases such as sodium hydroxide, potassium hydroxide, sodium carbonate and potassium carbonate. Of these, monoethanolamine is preferred from the viewpoint of dyeing power.

These alkali agents may be used either singly or in combination of two or more. Their content in the hair dye composition of the present invention is preferably from 0.01 to 20 wt. %, more preferably from 0.1 to 10 wt. % from the viewpoints of dyeing the hair into a non-reddish black color suited for covering up the Asian gray hair.

In the hair dye composition of the present invention, a silicone can be incorporated from the viewpoints of texture of foams, smooth touch of foams, reduction in friction between individual hairs during shampooing or washing, and smoothness during drying. Examples of such a silicone will next be given.

(1) Dimethylpolysiloxanes

Examples include those represented by the following formula:

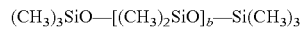

(wherein, b stands for a number from 3 to 20000).

(2) Amino-Modified Silicones

Various amino-modified silicones are usable, of which those listed in the INCI dictionary (International Cosmetic Ingredient Dictionary and Handbook/USA, 10th edition) under the name of Amodimethicone, Aminoethyl aminopropyl Dimethicone or Aminopropyl Dimethicone and having an average molecular weight from about 3000 to 100000 are preferred. These amino-modified silicones are used preferably in the form of an aqueous emulsion. They are commercially available, for example, as "SM 8704C" (product of Dow Corning Toray), "DC 929" (product of Dow Corning) and "KT 1989" (product of GE Toshiba). Although no particular limitation is imposed on the N content, it is preferably from 0.01 to 1 wt. %, more preferably from 0.05 to 0.3 wt. %.

(3) Other Silicones

Examples of silicones other than the above-described ones include polyether-modified silicones, methylphenylpolysiloxanes, fatty acid-modified silicones, alcohol-modified silicones, alkoxy-modified silicones, epoxy-modified silicones, fluorine-modified silicones, cyclic silicones and alkyl-modified silicones.

These silicones may be used either singly or in combination of two or more and their content in the hair dye composition of the present invention is preferably from 0.01 to 10 wt. %, more preferably from 0.05 to 6 wt. %, even more preferably from 0.3 to 3 wt. %.

In the hair dye composition of the present invention, an oil agent can be incorporated further as another conditioning agent. Examples of the oil agent include hydrocarbons such as squalene, squalane, liquid paraffin, liquid isopraffin, and cycloparaffin; glycerides such as castor oil, cacao oil, mink oil, avocado oil and olive oil; waxes such as beeswax, spermaceti, lanolin and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearyl acid, and isopalmitic acid; unsaturated or branched higher alcohols; and other oil agents such as isostearyl glyceryl ether and polyoxypropylene butyl ether. These oil agents may be used either singly or in combination of two or more. Their content in the hair dye composition of the present invention is preferably from 0.2 to 2 wt. %, more preferably from 0.3 to 1.8 wt. %, even more preferably from 0.5 to 1.5 wt. %.

In the hair dye composition of the present invention, components typically employed for hair dyes can be incorporated in addition to the above-described components. For example, an aqueous medium, stabilizer, buffer, perfume, touch improver, chelating agent, solubilizing agent, preservative and the like can be added as needed, depending on the purpose of use.

The melanin precursor as Component (A) reacts with oxygen in the air under basic conditions and is converted into a melanin pigment. The hair dye composition of the present invention is therefore adjusted to a pH ranging from 8 to 11, preferably from 9 to 11.

The hair dye composition of the present invention is preferably provided in the form of an aerosol in order to maintain its dyeing power even after repeated use or improve the dyeing power. An aerosol can be produced by filling a pressure container (aerosol can or the like) with the hair dye composition of the present invention as a stock solution of aerosol together with a propellant.

As the propellant, compressed gas and liquefied gas commonly used for aerosol products are usable. Examples of the compressed gas include nitrogen gas, carbon dioxide gas, and argon gas, while those of the liquefied gas include liquefied petroleum gas, volatile $C_{3-5}$ hydrocarbons and dimethyl ether. Two or more propellants may be used in combination. In order to attain an adequate injection speed, it is preferred to incorporate the propellant(s) in an amount from 1 to 20 wt. %, more preferably from 3 to 15 wt. % based on the entire composition composed of a stock solution and the propellant(s). In addition, the internal pressure of the aerosol can filled with them is preferably controlled to fall within from 0.3 to 0.5 MPa (25° C.)

When the composition is filled in a container, clinching and deaeration are carried out simultaneously to reduce the air remaining inside the container. Such a deaeration operation is effective for stabilizing the content in the container. For example, the deaeration operation is performed preferably under a pressure not greater than 48 kPa.

The hair dye composition of the present invention can of course be used at room temperature, but the dyeing power is improved when heat and oxygen are supplied by a drier.

EXAMPLES

Examples 1 to 4

An aerosol type one-part hair dye composition was obtained by preparing a stock solution of the aerosol type one-part hair dye composition in accordance with the formulation shown in Table 1, filling the stock solution in an aerosol test bottle (product of Tokyo Koubunshi Corporation), clinching the bottle, and filling 0.35 MPa of a liquefied petroleum gas:dimethyl ether mixture (weight ratio=90:10) as a propellant to give a stock solution:gas ratio of 90:10 (weight ratio).

The aerosol type one-part hair dye compositions thus obtained were tested and evaluated as described below and the results are shown in Table 1.

Dyeing Property (ΔE):

Each of the aerosol type hair dye compositions (1 g) was applied to about 1 g of a tress of the dry white hair obtained from a Chinese woman. After the resulting hair tress was left to stand for 5 minutes at room temperature, it was shampooed and washed with water. The dyeing operation was repeated three times and white-hair dyeing property (ΔE, Minolta CR300) of the compositions and final hair color were evaluated.

By the above-described dyeing operation, the tress of white hair was dyed into a slightly reddish brown color in Example 1, a slightly bluish dark gray color in Example 2, a brown color in Example 3, and a bluish gray color in Example 4. A change in hair color due to a change in the combination ratio of antioxidants was thus confirmed.

Storage Stability

Each aerosol type hair dye composition was filled in an aerosol container. After storage for one month at 40° C., appearance, injection performance, and hair dyeing properties of each composition were evaluated by comparing them with those just after preparation. As a result, each composition showed almost no change in the appearance, injection performance and dyeing properties.

TABLE 1

|     | Raw materials | Formulation of stock solution (wt. %) Examples | | | |
|-----|---------------|---|---|---|---|
|     |               | 1 | 2 | 3 | 4 |
| (A) | Aqueous 5,6-Dihydroxyindole solution | 0 | 0 | 0 | 0 |
|     | 5,6-Dihydroxyindoline-2-carboxylic acid | 0 | 0 | 0.3 | 0.3 |
|     | 5,6-Dihydroxyindole and 5,6-dihydroxyindole-2-carboxylic acid mixture (molar ratio: 90:10) | 0.3 | 0.3 | 0 | 0 |

TABLE 1-continued

|  | Raw materials | Formulation of stock solution (wt. %) Examples | | | |
| --- | --- | --- | --- | --- | --- |
|  |  | 1 | 2 | 3 | 4 |
| (B) | Ascorbic acid | 0.3 | 0.1 | 0.3 | 0.05 |
|  | Sodium sulfite | 0.05 | 0.3 | 0.05 | 0.3 |
| (C) | Polyoxyethylene tridecyl ether ("Softanol 90", product of Nippon Shokubai) | 1.5 | 1.5 | 1.5 | 1.5 |
| (D) | Hydroxypropyl xanthan gum ("Rhaball gum EX", product of Dainippon Sumitomo Pharma) | 0.3 | 0.3 | 0.3 | 0.3 |
| Others | 95 vol. % Ethanol | 10 | 10 | 20 | 20 |
|  | Ethanolamine | 0.5 | 0.5 | 0.1 | 0.1 |
|  | Sodium hydroxide | q.s. | q.s. | q.s. | q.s. |
|  | Citric acid | q.s. | q.s. | q.s. | q.s. |
|  | Water | Balance | Balance | Balance | Balance |
|  | Total | 100 | 100 | 100 | 100 |
|  | Molar ratio (ascorbic acid/sodium sulfite) | 78/22 | 16/84 | 78/22 | 9/91 |
|  | pH | 10 | 10 | 10 | 10 |
|  | Viscosity (mPa·s) at 25° C. | 400 | 400 | 400 | 400 |
| Evaluation | Dyeing property (ΔE) after three-time hair dyeing treatments | 40 | 40 | 30 | 30 |
|  | Storage stability | Good | Good | Good | Good |
|  | Color tone | Brownish | Bluish | Brownish | Bluish |

The invention claimed is:

1. A one-part hair dye composition comprising the following components (A) to (D):
   (A) one or two or more compounds represented by the following formula (1):

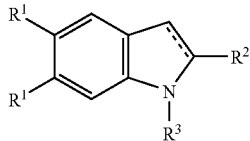

wherein, a broken line represents the presence or absence of a π bond, $R^1$ represents a hydroxy group or acetoxy group, $R^2$ represents a hydrogen atom, —COOR (wherein, R represents a hydrogen atom, a methyl group or an ethyl group) or —COO$^-$X$^+$ (wherein, X$^+$ represents a cation), and $R^3$ represents a hydrogen atom, an acetyl group, a methyl group or an ethyl group;
   (B) an antioxidant composed of a combination of ascorbic acid or salt thereof and sulfurous acid or salt thereof;
   (C) a nonionic surfactant; and
   (D) a thickening polymer, wherein the composition has a pH of 8 to 11.

2. The one-part hair dye composition according to claim 1, wherein the total content of Component (B) is from 0.01 to 5 wt. %.

3. The one-part hair dye composition according to claim 1, further comprising monoethanolamine, wherein the composition has a pH of from 9 to 11.

4. The one-part hair dye composition according to claim 1, wherein Component (A) comprises at least 5,6-dihydroxyindole and 5,6-dihydroxyindole-2-carboxylic acid.

5. The one-part hair dye composition according to claim 4, wherein a molar ratio of 5,6-dihydroxyindole to 5,6-dihydroxyindole-2-carboxylic acid is from 50:50 to 999:1.

6. A method of controlling hair color, comprising, dyeing hair with a one-part hair composition as claimed in any one of claims 1 to 5.

7. The one-part hair dye composition according to claim 2, further comprising monoethanolamine, wherein the composition has a pH of from 9 to 11.

8. The one-part hair dye composition according to any one of claim 2, 3 or 7, wherein Component (A) comprises at least 5,6-dihydroxyindole and 5,6-dihydroxyindole-2-carboxylic acid.

9. The one-part hair dye composition according to claim 8, wherein a molar ratio of 5,6-dihydroxyindole to 5,6-dihydroxyindole-2-carboxylic acid is from 50:50 to 999:1.

10. A method of controlling hair color, comprising, dyeing hair with a one-part hair dye composition as claimed in claim 9.

11. The method of claim 6, wherein the molar ratio of said (ascorbic acid or salt thereof)/(sulfurous acid or salt thereof) in Component (B) of said composition is 99/1 to 50/50.

12. The method of claim 10, wherein the molar ratio of said (ascorbic acid or salt thereof)/(sulfurous acid or salt thereof) in Component (B) of said composition is 99/1 to 50/50.

13. The method of claim 6, wherein the molar ratio of said (ascorbic acid or salt thereof)/(sulfurous acid or salt thereof) in Component (B) of said composition is 49/51 to 31/69.

14. The method of claim 6, wherein the molar ratio of said (ascorbic acid or salt thereof)/(sulfurous acid or salt thereof) in Component (B) of said composition is 30/70 to 1/99.

15. The method of claim 10, wherein the molar ratio of said (ascorbic acid or salt thereof)/(sulfurous acid or salt thereof) in Component (B) of said composition is 49/51 to 31/69.

16. The method of claim 10, wherein the molar ratio of said (ascorbic acid or salt thereof)/(sulfurous acid or salt thereof) in Component (B) of said composition is 30/70 to 1/99.

* * * * *